United States Patent [19]

Yoshinaka et al.

[11] 4,328,374

[45] May 4, 1982

[54] PROCESS FOR THE PRODUCTION OF AROMATIC DIALDEHYDES

[75] Inventors: Shigeo Yoshinaka; Masaharu Dōya, both of Niigata, Japan

[73] Assignee: Mitsubishi Gas Chemical Co., Inc., Tokyo, Japan

[21] Appl. No.: 166,114

[22] Filed: Jul. 7, 1980

[30] Foreign Application Priority Data

Jul. 5, 1979 [JP] Japan .................................. 54-85432

[51] Int. Cl.$^3$ ............................................. C07C 45/28
[52] U.S. Cl. .................................... 568/436; 568/437; 562/410
[58] Field of Search ............................... 568/436, 437

[56] References Cited

U.S. PATENT DOCUMENTS 2,948,756 8/1960 Bengelsdorf ....................... 568/437

FOREIGN PATENT DOCUMENTS 1229061 6/1967 Fed. Rep. of Germany .
39-26962 11/1964 Japan ................................... 568/436
1473935 5/1977 United Kingdom .

OTHER PUBLICATIONS

Migrdichian, Organic Synthesis, vol. 2, (1957), 1331.
Patai, The Chemistry of the Carbonyl Group (1966), 181–183.
CA 53 1222$^a$–Preparation of m–phthalic dialdehyde dated 1959 at p. 1222.
CA 65 5405$^b$–Terephthaldialdehyde dated 1966 at p. 5405.

*Primary Examiner*—Bernard Helfin
*Attorney, Agent, or Firm*—Wenderoth, Lind & Ponack

[57] ABSTRACT

A process for the production of aromatic dialdehydes which comprises reacting xylene chloride selected from the group consisting of α,α,α'-trichloroxylene alone, or a mixture of α,α,α'-trichloroxylene and α,α'-dichloroxylene, a mixture of α,α,α'-trichloroxylene and α,α,α',α'-tetrachloroxylene and a mixture of α,α,α'-trichloroxylene, α,α'-dichloroxylene and α,α,α',α'-tetrachloroxylene with nitric acid.

3 Claims, No Drawings

PROCESS FOR THE PRODUCTION OF AROMATIC DIALDEHYDES

The present invention relates to a process for the production of aromatic dialdehydes. More particularly, it relates to a process for the production of aromatic dialdehydes which comprises reacting, α,α,α'-trichloroxylene or α,α,α'-trichloroxylene-based chloroxylene mixtures with nitric acid.

Aromatic dialdehydes are well known to be valuable as intermediate materials for various polymers, agricultural chemicals, pharmaceuticals, dyestuffs and varieties of other industrial chemicals.

Conventionally a number of processes are known as process for the production of aromatic dialdehydes. There are known processes, for the production of aromatic dialdehydes such as substituting halogen atoms respectively for two hydrogen atoms of the respective methyl groups of xylene, followed by hydrolysis [C.A. 53 1222$^a$, Belgian Pat. No. 667022(1965) and British Pat. No. 1,473,935]; reducing aromatic dicarboxylic acid dichloride (German Pat. No. 2556206, Japanese Laid-Open Application No. 53-23913); directly oxidizing side chains of xylene (U.S. Pat. No. 3,597,485) or oxidizing bischloromethylbenzenes (U.S. Pat. No. 2,948,756 and German Pat. No. 1229061) and so on. These preparative processes, however, do not necessarily bring about favorable results, entailing various shortcomings. In the case of the process of preparing α,α,α',α'-tetrahalogenoxylene by substituting halogens for two hydrogen atoms in the respective methyl groups of xylene, followed by hydrolysis, difficulty lies in in obtaining starting material α,α,α',α'-tetrahalogenoxylene. That is, when preparing α,α,α',α'-tetrahalogenoxylene, xylene is usually halogenated, but in this halogenation step it is difficult to selectively synthesize α,α,α',α'-tetrahalogenoxylene and products are obtained as mixtures of various halogenoxylenes with different halogenation degrees. If it is intended to separate α,α,α',α'-tetrahalogenoxylene from these mixtures by distillation, its separation is difficult because boiling points of α,α,α',α'-tetrahalogenoxylene come close to those of other halogenoxylenes in the mixtures and it cannot be said economical. If the intended substance is α,α,α',α'-tetrahalogeno-p-xylene, it is possible to selectively crystallize and filter it off from the mixtures, but this process entails such drawbacks that yield is not always good whereas with meta-isomer and ortho-isomer their separation is not always effected in good condition.

The process for reduction of aromatic dicarboxylic acid dichloride can hardly be said a favorable process since starting material is high in costs and because it is necessary to use expensive palladium type catalysts and yield is not always high. The liquid phase process and gas phase process are known for the process for the production of aromatic dialdehyde by directly oxidizing methyl groups of xylene. In the case of the liquid phase process, for one thing, methyl groups of xylene are oxidized by the use of chromium trioxide, but even with this process yield is not necessarily high and added to this, many secondary materials are required and it cannot be said a commercially practical process.

With the gas phase process favorable results are not achieved in terms of selectivity.

As the process being relatively good in selectivity is known the process of the U.S. Pat. No. 3,597,485. This process comprises oxidizing alkylbenzene in gas phase in the presence of mixed catalyst consisting of tungsten and molybdenum oxides and terephthalaldehyde is obtained in 40–60% yield by passing air containing about 1% of p-xylene over the catalyst heated at 475°–575° C. with the contact set at 0.1–0.2 seconds. In this process, however, difficulty lies in recovery of products since dilute xylene is oxidized. On top of that, sublimation and reduction of effective components of catalyst cause a great lowering of catalyst activity and it is difficult to use it on a commercial basis unless these problems are solved. As the process for the production of aromatic dialdehydes using bishalomethylbenzene as starting material there are known, for instance, a preparative process of being acted upon with urotropin, air oxidation process and process of oxidizing with pyridine-N-oxide, but either of these processes is low in yield, involving use of a great deal of secondary material, and it cannot be said a practical process. Of processes using bischloromethylbenzene as starting material it is those processes involving the using, as the oxidizing agent, of nitric acid that achieved relatively favorable results. The U.S. Pat. No. 2,948,756 or West German Pat. No. 1229061, for instance, is known. The U.S. Pat. No. 2,948,756 comprises oxidizing p-xylene dichloride (viz., α,α'-dichloro-p-xylene) with nitric acid in a concentration of 10–19% at temperatures of 102°–110° C., nitric acid being used in the amount of 2–50 mols per mole of p-xylene dichloride, and terephthalaldehyde is obtained in 30–70% yield. West German Pat. No. 1229061 is an improvement of the U.S. Pat. No. 2948756 and follows procedures of oxidizing halomethylbenzenes with dilute nitric acid in the presence of heavy metal compound catalyst and terephthalaldehyde is obtained in 70–87% yield. As mentioned above, of conventional techniques relatively favorable results are obtained with the process of oxidizing p-xylene dichloride with nitric acid, but even with this process difficulty lies in economically obtaining starting material xylene dichoride. That is, xylene dichloride is usually prepared by the chlorination reaction of xylene, but in that case, it is difficult to selectively synthesize xylene dichloride and products are obtained as mixtures with different chlorination degrees of compounds or isomers. It is relatively easy to separate xylene dichloride from this mixture by distillation, but it entails such drawbacks as to form α,α-dichloroxylene, an isomer of xylene dichloride, as by-product, during the chlorination reaction of xylene, the amount of α,α-dichloroxylene formed as by-product amounting to 0.25–0.35 parts by weight per part by weight of α,α'-dichloroxylene. As mentioned thus far, prior art techniques for the process for the production of aromatic dialdehydes entail various shortcomings.

Therefore, the purpose of the present invention is to provide a process for the production of aromatic dialdehydes from readily available starting material in good yield, removing the said drawbacks with prior art techniques.

The instant inventors studied hard in order to achieve the said objective, in consequence of which it was found that aromatic dialdehydes could be produced in good yield from α,α,α'-trichloroxylene or from mixtures of α,α,α'-trichloroxylene, as the main component, with α,α'-dichloroxylene, α,α,α',α'-tetrachloroxylene or mixtures thereof, ending in accomplishment of the process of the present invention.

That is, the purpose of the present invention can be achieved by reacting with nitric acid α,α,α'-trichloroxylene alone, or a chloroxylene mixture selected from the group consisting of a mixture of α,α,α'-trichloroxylene and α,α'-dichloroxylene, a mixture of α,α,α'-trichloroxylene and α,α,α',α'-tetrachloroxylene and a mixture of α,α,α'-trichloroxylene, α,α'-dichloroxylene and α,α,α',α'-tetrachloroxylene.

In the present invention pure α,α,α'-trichloroxylene can be used in the reaction. Usually, however, α,α,α'-trichloroxylene, as mentioned in detail hereinafter, is prepared by chlorinating the methyl groups of xylene and on that occasion, either or both of α,α'-dichloroxylene and α,α,α',α'-tetrachloroxylene are formed as by-products in various proportions according to reaction conditions and reaction products containing these by-products can be conveniently used as such. These reaction products contain small amounts of other by-products, such as pentachloroxylene and so on, as the case may be, but usually they can be used as such without removing these ones.

In the production of α,α,α'-trichloroxylene by the chlorination of methyl groups of xylene, isomers are formed in less amounts as compared to the case for the production of xylene dichloride and it is more easy to separate from other chlorides on the occasion of distillation compared to the case for the production of α,α,α',α'-tetrachloroxylene. By distilling the reaction mixture as formed it is possible to separate and use as α,α,α'-trichloroxylene, a mixture of α,α,α'-trichloroxylene and α,α'-dichloroxylene, a mixture of α,α,α'-trichloroxylene and α,α,α',α'-tetrachloroxylene or a mixture of α,α,α'-trichloroxylene, α,α'-dichloroxylene and α,α,α',α'-tetrachloroxylene (these mixtures will be called chloroxylene mixtures in the instant specification).

After separating by distillation as single compounds α,α'-dichloroxylene and α,α,α',α'-tetrachloroxylene can also be used by mixing to other chloroxylenes in such a manner as to form chloroxylene mixtures with composition proportions as desired.

Preferred compositions of chloroxylene mixtures are 20-45 mol % α,α'-dichloroxylene, 55-35 mol % α,α,α'-trichloroxylene and 45 mol % or less α,α,α',α'-tetrachloroxylene.

In the process of the present invention α,α,α'-trichloroxylene, α,α'-dichloroxylene and α,α,α',α'-tetrachloroxylene mean xylene chlorides represented by following formulae:

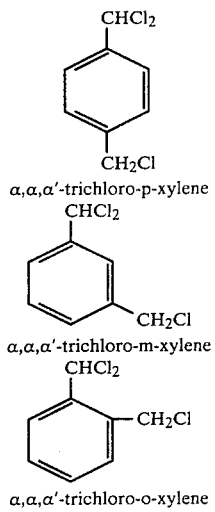

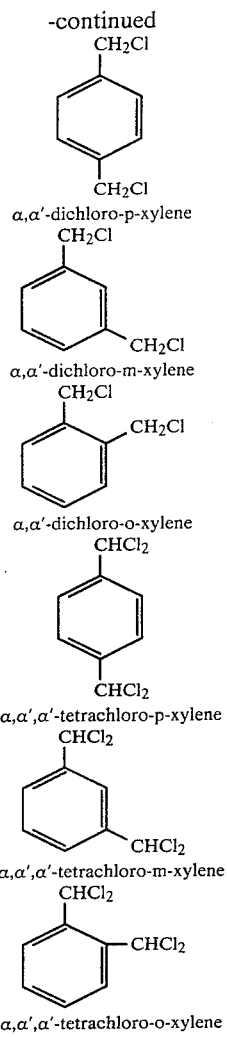

Aromatic dialdehyde mean terephthalaldehyde, isophthalaldehyde and phthalaldehyde.

The said production of α,α,α'-trichloroxylene by the chlorination of the methyl groups of xylene is usually conducted by following the procedures of bubbling chlorine in the liquid phase under the irradiation of ultraviolet ray-containing light or mixing or bubbling chlorine in the liquid phase by the addition of radical generators, such as benzoyl peroxide, azobisisobutyronitrile and so on, to the reaction solution. In those cases, it is not always necessary to use reaction solvents, but it is, of course, possible to use hydrocarbon chloride solvents, such as carbon tetrachloride and so on. The chlorination reaction is carried out usually at reaction temperatures of 50°-C.-160° C. and preferably 70° C.-140° C., but actual reaction temperatures are optionally selected according to the presence of solvent, its kind and kind of xylene being chlorinated. The time for the chlorination reaction can be optionally determined according to the chlorine blow method. In the said process for the production of α,α,α'-trichloroxylene or chloroxylene mixtures by the chlorination reaction of xylene the reaction could be conducted, as the case may be, by the addition of alkylene polyamine, benzamide, triarylphosphate and so forth for inhibition of undesirable impurities. The chlorination reaction could be carried out either by the batchwise process or by the continuous process. What is important for the chlorination reaction is a molar ratio of chlorine and xylene to react and it is necessary to react 2-4 mols of chlorine per mol of xylene for the production of chloroxylene mixtures having 2-4 chlorine atoms on the average in the side chains per molecule of xylene.

The reaction of xylene with chlorine can be conducted nearly quantitatively and it is possible to obtain chloroxylene mixtures with the intended average chlorination degree by reacting with xylene chlorine in the amount substantially equal to the amount corresponding to the intended average chlorination degree of chloroxylene mixtures or a slight excess of chlorine. In this case, if the amount of chlorine to react is less with regard to the amount of xylene, the amount of chloroxylene with a low chlorination degree, such as α-chloroxylene or α,α-dichloroxylene, in the reaction product goes higher, causing an excessive lowering of the average chlorination degree of chloroxylene mixtures, ending occasionally in having less than 2 chlorine atoms on the average per molecule of xylene. If the amount of chlorine to react is too great, the amount of chloroxylene with a high chlorination degree, such as α,α,α,α',α'-pentachloroxylene and α,α,α,α',α'-hexachloroxylene, in the product goes higher, overly increasing the average chlorination degree of chloroxylene mixtures, ending occasionally in having chlorine atoms in excess of 4 on the average per molecule of xylene. It is not preferred. These compounds, such as low chloroxylene mixtures or high chloroxylene mixtures form, in the subsequent reaction with nitric acid, various compounds other than the intended aromatic dialdehydes as represented by following formulae, resulting in a lowering of yield of aromatic dialdehydes:

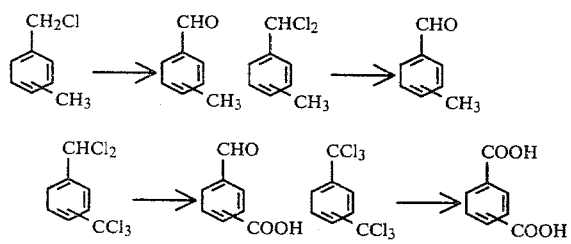

For the molar ratio of chlorine and xylene to react, therefore, it is important to set the amount of chlorine generally at 2-4 mols per mol of xylene and it is particularly preferred to set the average chlorination degree of chloroxylene mixtures at 2.5-3.5.

The average chlorination degree is defined as:

$$\frac{\text{Mol numbers of chlorines introduced}}{\text{Mol numbers of xylenes}}$$

α,α,α'-Trichloroxylene or chloroxylene mixtures used in the process of the present invention can readily be prepared as the above.

The process of the present invention can be carried out by mixing α,α,α'-trichloroxylene or chloroxylene mixtures obtained as the above and nitric acid in predetermined concentrations and reacting the mixture with stirring. Reactions of the respective xylenes with nitric acid are thought to proceed through hydrolysis and oxidation as shown by following formulae:

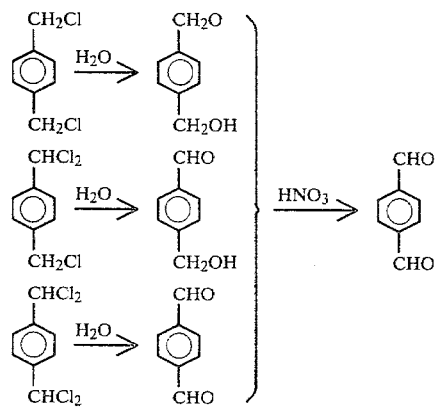

In effect, these reactions, viz., hydrolysis and oxidation, are considered to occur simultaneously. However, it is also possible to make these reactions proceed separately, vix., to hydrolyze α,α,α'-trichloroxylene or α,α,α',α'-tetrachloroxylene prior to reaction caused by the addition of nitric acid.

The concentration of nitric acid when the process of the present invention is carried out is generally 0.5-15% by weight, preferably 2-8% by weight and most preferably 3% or thereabout. If the concentration of nitric acid goes more high, it unpreferably tends to go high in the amount of carboxylic acids formed as by-products. If the concentration of nitric acid is lowered, on the other hand, it unpreferably goes inferior in the efficiency of the reaction, losing economical nature.

The reaction temperature in the reaction of α,α,α'-trichloroxylene or chloroxylene mixtures with nitric acid is generally 70° C. to 100° C. at normal pressure, and under pressure it is at conditions of 70°-130° C. at 3 kg/cm² or less. The most preferred reaction temperature, under normal pressure, is a temperature on the occasion of refluxing the reaction mixture in which α,α,α'-trichloroxylene or chloroxylene mixture and aqueous nitric acid solution were mixed and this temperature is about 100° C. or somewhat higher. This temperature somewhat varies according to the concentration of nitric acid and kind or relative amount of the reactant. The amount of nitric acid used is generally 0.2-20 mols and preferably 1.5-10 mols per mol of α,α,α'-trichloroxylene or chloroxylene mixtures. Selectivity to aromatic dialdehydes is, in general, improved if nitric acid is used in great amounts, but it is economically insignificant to use it in too great amounts.

The amount of nitric acid used is optionally determined according to the kind and composition of the substance to react with nitric acid and reaction conditions, but favorable results can be obtained by using nitric acid in great amounts if proportions of α,α'-dichloroxylene in chloroxylene mixtures are high. Nitric acid can be used in less amounts if proportions of α,α,α',α'-tetrachloroxylene are high.

Catalyst is not always required in the case of carrying out the process of the present invention, but the use of catalyst is a preferred mode of practice in that the reaction time is cut short when it is used. Compounds of metals of atomic numbers 23-29, such as their nitrates, chlorides, sulphates, oxides, carbonates and so on, are used for the catalyst in the process of the present invention, but of these compounds it is vanadium compounds, such as vanadium pentoxide, vanadium chloride, vanadyl sulphate or ammonium metavanadate, that are particularly preferred in terms of effect. The amount of catalyst added is optionally determined according to the kind of catalyst and concentration of nitric acid used, but it is usually 0.002–0.10 part by weight and preferably 0.01–0.06 part by weight, per part by weight of $\alpha,\alpha,\alpha'$-trichloroxylene or chloroxylene mixtures. Furthermore, mineral acids, such as hydrochloric acid and sulphuric acid are also effective as catalyst. The amount of mineral acid added in that case is 0.01–1.5 parts by weight and preferably 0.5–1.0 part by weight, per part by weight of $\alpha,\alpha,\alpha'$-trichloroxylene or chloroxylene mixtures. The reaction time differs according to the presence of catalyst and the amount of it used, but it is generally 3–10 hours and preferably 4–8 hours in the case of using catalyst. The reaction time in the case of using no catalyst is generally 10–20 hours and preferably 15 hours or more.

In the practice of the process of the present invention, $\alpha,\alpha,\alpha'$-trichloroxylene, chloroxylene mixtures, reaction intermediates or intended aromatic dialdehydes occasionally adhere as crystals to the space walls and condensor of the reactor, forming bars to the practice of the process of the present invention, but these bars could possibly be avoided by the addition of small amounts of organic solvents. As the organic solvents in that case are preferred those which do not transform themselves by the reaction with the substances present in the reaction system during the reaction, such as aromatic hydrocarbons, such as benzene, toluene, xylene and so on, $C_6$–$C_9$ aliphatic hydrocarbons, $C_4$–$C_6$ ketones or $C_5$–$C_8$ ethers, etc. The kinds and amounts of these solvents added are optionally selected according to reaction conditions, but usually the amounts of the solvents added are 0.01–0.2 part by weight per part by weight of $\alpha,\alpha,\alpha'$-trichloroxylene or chloroxylene mixtures and it is not preferred to use the solvents in as great amounts as more than necessary because it ends sometimes in increasing amounts of carboxylic acids and so forth formed as by-products.

It is not specifically necessary to add surface active agent in the case of carrying out the process of the present invention, but it is, of course, possible to conduct the reaction by the addition of the surface active agent. The process of the present invention could be carried out either by the batchwise process or by the continuous process.

The separation of the intended product from the reaction mixture obtained by the process of the present invention is effected by following normal procedures. That is, aromatic dialdehydes could be separated from the reaction product by filtering off crystals formed on cooling the reaction mixture after the reaction is complete or by extracting by the addition of organic solvent to the reaction product. The aromatic dialdehydes so separated occasionally contain carboxylic acids, etc. formed as by-products, but these acidic substances are removed by cleansing with dilute aqueous alkali solution. The aromatic dialdehydes obtained as the above are of high purity and can be used as such according to usage, but it is also possible to further purify them, if necessary, by following the usual purification procedures, such as distillation or recrystallization.

It is possible to recover free carboxylic acids, such as carboxybenzaldehyde, formed as by-products from the alkali cleansed part by following normal procedures. According to the process of the present invention aromatic dialdehydes could be prepared with much ease as well as in high yield as compared to prior art processes by the reaction of $\alpha,\alpha,\alpha'$-trichloroxylene or chloroxylene mixtures readily available by the chlorination of the side chain of xylene with nitric acid. By recovering carboxylic acids of commercially high utility value formed as by-products during the reaction the process for the production of aromatic dialdehydes could be made more advantageous.

In the next place, the process of the present invention will be explained by way of working examples, but the process of the present invention will in no way be limited by these examples.

EXAMPLE 1

Charged into a 2 l three neck distillation flask equipped with a thermometer, stirrer and reflux condensor were 84 g (0.40 mol) of $\alpha,\alpha,\alpha'$-trichloro-p-xylene, 1700 g of 3% by weight of nitric acid, 2.5 g of vanadium pentoxide and 3 ml of toluene and the temperature of the mixture was enhanced with stirring to cause the reaction under refluxed condition for 8 hours.

After the reaction was finished, the reaction product was cooled and crystals formed were filtered off. Then, crystals so filtered off were cleansed with 10% by weight of aqueous sodium bicarbonate solution for about 10 minutes. By cleansing carboxylic acid formed as by-product on the occasion of reaction moved into the cleansing solution.

Crystals left over undissolved on the occasion of cleansing were filtered off, washed with water and dried. Crystals obtained weighed 46.9 g. This one was identified as terephthalaldehyde by infrared absorption spectral analysis. It corresponds to 87.3% in the yield based on $\alpha,\alpha,\alpha'$-trichloro-p-xylene. It was analyzed by gas chromatography, in consequence of which it was of 99.6% purity.

Aqueous sodium bicarbonate solution obtained by cleansing crystals was acidified by the addition of mineral acid to give crystals. The crystals were filtered off, washed with water and dried to give 6.5 g of white substance. It was analyzed by infrared absorption spectra, in consequence of which this one was identified as 4-carboxybenzaldehyde.

EXAMPLE 2

Charged into the same reactor as used in Example 1 were 84 g (0.40 mol) of $\alpha,\alpha,\alpha'$-trichloro-p-xylene, 1700 g of 6% by weight of nitric acid and 3 ml of toluene and the temperature of the mixture was enhanced by heating with stirring to cause the reaction under refluxed condition for 15 hours.

By treating likewise as in Example 1 after the reaction was complete there was obtained 42.0 g of terephthalaldehyde. It corresponds to 78.2% based on $\alpha,\alpha,\alpha'$-trichloro-p-xylene charged. Further, by treating likewise as in Example 1 there was obtained 10.8 g of carboxylic acid as by-product.

EXAMPLE 3

Charged into the same reactor as used in Example 1 were 84 g of $\alpha,\alpha,\alpha'$-trichloro-p-xylene, 1700 g of mixed aqueous solution of 3% by weight of nitric acid and 5% by weight of hydrochloric acid and 3 ml of p-xylene and the temperature of the mixture was enhanced by heating with stirring to cause the reaction under refluxed condition for 6 hours. By treating likewise as in Example 1 after the reaction was complete there were obtained 43.0 g of terephthalaldehyde and 10.3 g of carboxylic acid as by-product. Yield of terephthalaldehyde was 80.0% based on α,α,α'-trichloro-p-xylene.

EXAMPLE 4

Charged into the same reactor as used in Example 1 were 84 g of α,α,α'-trichloro-m-xylene, 1700 g of 4% by weight of nitric acid, 2.8 g of ammonium metavanadate and 2 ml of m-xylene and the temperature of the mixture was enhanced by heating with stirring to cause the reaction under refluxed condition for 8 hours.

By treating likewise as in Example 1 after the reaction was complete there was obtained 45.6 g of isophthalaldehyde. It corresponds to 84.9% in the yield based on α,α,α'-trichloro-m-xylene charged. This one was analysed by gas chromatography, in consequence of which it was of 99.7% purity.

EXAMPLE 5

Charged into the same reactor as used in Example 1 were 63.0 g of α,α,α'-trichloro-m-xylene, 1700 g of 5% by weight of aqueous nitric acid solution, 5.0 g of Cu(NO$_3$)$_2$.3H$_2$O and 2 ml of toluene and the temperature of the mixture was enhanced by heating with stirring to cause the reaction under refluxed condition for 10 hours.

By treating likewise as in Example 1 after the reaction was complete there was obtained 32.3 g of isophthalaldehyde. It corresponds to 80.2% in the yield based on α,α,α'-trichloro-m-xylene charged.

EXAMPLE 6

Charged into the same reactor as used in Example 1 were 230 g of α,α,α'-trichloro-o-xylene, 1700 g of 8% by weight of nitric acid and 6 g of vanadium pentoxide and the temperature of the mixture was enhanced by heating with stirring to cause the reaction under refluxed condition for 5 hours.

After the reaction was complete, the reaction product was cooled and subjected to 4 times of extraction operations by the addition of 300 g of toluene for each time. Toluene obtained by the extraction operations was put together and it was cleansed with aqueous sodium bicarbonate solution and then toluene was distilled off. After the distillation of toluene 119.5 g of residue was obtained. This one was distilled under reduced pressure of 10 mmHg to give 112 g of somewhat yellowish crystals. This one was identified as phthalaldehyde by infrared absorption spectral analysis. Yield of phthalaldehyde was 76% based on α,α,α'-trichloro-o-xylene.

EXAMPLE 7

Charged into the same reactor as used in Example 1 were 97.0 g of chloroxylene mixture with a composition of 45.4% by weight (44.0 g, 0.25 mol) of α,α'-dichloro-p-xylene and 54.6% by weight (53.0 g, 0.25 mol) of α,α,α'-trichloro-p-xylene, 1580 g of 4% by weight of nitric acid, 3 g of vanadium pentoxide and 3 ml of toluene and the temperature of the mixture was enhanced by heating with stirring to cause the reaction under refluxed condition for 6 hours.

After the reaction was complete, the reaction product was cooled and crystals so formed were filtered off. The crystals so filtered off were cleansed with 10% by weight of aqueous sodium bicarbonate solution for about 10 minutes. On that occasion, carboxylic acid formed as by-product moved into the cleansing water and terephthalaldehyde remained undissolved in water. Crystals obtained were filtered off, washed with water and then dried.

Crystals so obtained weighed 59.0 g. This one was analysed by infrared absorption spectra, in consequence of which it was identified as terephthalaldehyde. Further, the purity by the analysis of gas chromatography was 99.7%. Yield of terephthalaldehyde was 88% based on α,α'-dichloro-p-xylene and α,α,α'-trichloro-p-xylene charged.

Crystals obtained by filtering off the reaction product were cleansed with aqueous sodium bicarbonate solution and aqueous alkali solution occurred on that occasion was acidified by the addition of mineral acid to precipitate crystals. The resultant crystals were filtered off, washed with water and then dried to give 6.0 g of white crystals. It was analyzed by infrared absorption spectra, in consequence of which this one was identified as 4-carboxybenzaldehyde.

EXAMPLE 8

Charged into the same reactor as used in Example 1 were 91.0 g of chloroxylene mixture with a composition of 46.2% by weight (42.0 g, 0.20 mol) of α,α,α'-trichloro-p-xylene and 53.8% by weight (49.0 g, 0.20 mol) of α,α,α'-tetrachloro-p-xylene, 1520 g of 2.5% by weight of nitric acid and 3 ml of p-xylene and the temperature of this mixture was enhanced with stirring to cause the reaction under refluxed condition for 15 hours. By treating likewise as in Example 1 after the reaction was complete there was obtained 43.1 g of terephthalaldehyde. It corresponds to 80.3% terephthalaldehyde yield based on α,α,α'-trichloro-p-xylene and α,α,α'-tetrachloro-p-xylene charged.

By treating likewise as in Example 1 there was obtained 5.4 g of carboxylic acid as by-product.

EXAMPLE 9

Charged into the same reactor as used in Example 1 were 84.5 g of chloroxylene mixture with a composition of 20.7% by weight (17.5 g, 0.1 mol) of α,α'-dichloro-p-xylene, 49.7% by weight (42.0 g, 0.2 mol) of α,α,α'-trichloro-p-xylene and 29.6% by weight (25.0 g, 0.10 mol) of α,α,α',α'-tetrachloro-p-xylene, 1700 g of 3% by weight of nitric acid, 3.0 g of ammonium metavanadate and 3 ml of p-xylene. The temperature of this mixture was enhanced by heating with stirring to cause the reaction under refluxed condition for 9 hours.

By treating likewise as in Example 1 after the reaction was complete there were obtained 46.9 g of terephthalaldehyde and 6.3 g of carboxylic acid as by-product.

Yield of terephthalaldehyde corresponds to 87.4% based on α,α'-dichloro-p-xylene, α,α,α'-trichloro-p-xylene and α,α,α',α'-tetrachloro-p-xylene charged.

EXAMPLE 10

Charged into the same reactor as used in Example 1 were 88.0 g of chloroxylene mixture with a composition of 10.2% by weight (9.0 g, 0.05 mol) of α,α'-dichloro-p-xylene, 47.7% by weight (42.0 g, 0.2 mol) of α,α,α'-trichloro-p-xylene and 42.1% by weight (37.0 g, 0.15 mol) of α,α,α',α'-tetrachloro-p-xylene, 1700 g of aqueous solution containing 3% by weight of nitric acid and 3% by weight of hydrogen chloride and 3 ml of p-xylene and the temperature of this mixture was enhanced by heating with stirring to cause the reaction under refluxed condition for 7 hours.

By treating likewise as in Example 1 after the reaction was complete there were obtained 43.3 g of terephthalaldehyde and 8.6 g of carboxylic acid as by-product.

Yield of terephthalaldehyde corresponds to 80.1% based on $\alpha,\alpha'$-dichloro-p-xylene, $\alpha,\alpha,\alpha'$-trichloro-p-xylene and $\alpha,\alpha,\alpha',\alpha'$-tetrachloro-p-xylene charged.

EXAMPLE 11

Charged into the same reactor as used in Example 1 were 84.5 g of chloroxylene mixture with a composition of 20.7% by weight (17.5 g, 0.1 mol) of $\alpha,\alpha'$-dichloro-m-xylene, 49.7% by weight (42.0 g, 0.2 mol) of $\alpha,\alpha,\alpha'$-trichloro-m-xylene and 29.6% by weight (25.0 g, 0.10 mol) of $\alpha,\alpha,\alpha',\alpha'$-tetrachloro-m-xylene, 1500 g of 3.5% by weight of nitric acid, 2.0 g of vanadium pentoxide and 3 ml of m-xylene and the temperature of this mixture was enhanced by heating with stirring to cause the reaction under refluxed condition for 8 hours.

By treating likewise as in Example 1 after the reaction was complete there was obtained 46.0 g of isophthalaldehyde. It corresponds to 85.8% in the yield based on $\alpha,\alpha'$-dichloro-m-xylene, $\alpha,\alpha,\alpha'$-trichloro-m-xylene and $\alpha,\alpha,\alpha',\alpha'$-tetrachloro-m-xylene.

EXAMPLE 12

Charged into the same reactor as used in Example 1 were 91.0 g of chloroxylene mixture with a composition of 46.2% by weight of $\alpha,\alpha,\alpha'$-trichloro-m-xylene and 53.4% by weight of $\alpha,\alpha,\alpha',\alpha'$-tetrachloro-m-xylene, 1700 g of 3% by weight of aqueous nitric acid solution, 5.0 g of $Cu(NO_3)_2.3H_2O$ and 3 ml of m-xylene and the temperature of the mixture was enhanced by heating with stirring to cause the reaction under refluxed condition for 10 hours.

By treating likewise as in Example 1 after the reaction was complete there was obtained 44.0 g of isophthalaldehyde. It corresponds to 82.1% in the yield based on chloroxylene mixture charged.

EXAMPLE 13

Charged into the same reactor as used in Example 1 were 84.5 g of chloroxylene mixture with a composition of 20.7% by weight of $\alpha,\alpha'$-dichloro-o-xylene, 49.7% by weight of $\alpha,\alpha,\alpha'$-trichloro-o-xylene and 29.6% by weight of $\alpha,\alpha,\alpha',\alpha'$-tetrachloro-o-xylene, 1660 g of 3.8% by weight of aqueous nitric acid solution and 2.5 g of vanadium pentoxide and the temperature of the mixture was enhanced by heating with stirring to cause the reaction for 8 hours.

After the reaction was complete, the reaction product was cooled and subjected to 4 times of extraction operations by the addition of 300 g of toluene for each time. Toluene obtained by the extraction operations was put together, it was cleansed with aqueous sodium bicarbonate solution and then toluene was distilled off. In this way there was obtained 45.0 g of residue. This one was analyzed by infrared absorption spectra, in consequence of which it was identified as phthalaldehyde.

Yield of phthalaldehyde corresponds to 84.0% based on chloroxylene mixture charged. Phthalaldehyde obtained was analyzed by gas chromatography, in consequence of which it was 99.6% purity.

EXAMPLE 14

Charged into the same reactor as used in Example 1 were 84 g of $\alpha,\alpha,\alpha'$-trichloro-p-xylene, 1700 g of 3% by weight of nitric acid, 3.0 g of vanadium pentoxide and 3 ml of toluene and the temperature of the mixture was enhanced by heating to cause the reaction with stirring at a temperature of about 90° C. for 10 hours.

By treating likewise as in Example 1 after the reaction was complete there were obtained 44.0 g of terephthalaldehyde and 7.8 g of carboxylic acid as by-product.

Yield of terephthalaldehyde was 82.1% based on $\alpha,\alpha,\alpha'$-trichloro-p-xylene charged.

EXAMPLE 15

Charged into the same reactor as used in Example 1 were 84.5 g of mixture with a composition of 20.7% by weight of $\alpha,\alpha'$-dichloro-p-xylene, 49.7% by weight of $\alpha,\alpha,\alpha'$-trichloro-p-xylene and 29.6% by weight of $\alpha\alpha\alpha',\alpha'$-tetrachloro-p-xylene, 1700 g of 3% by weight of nitric acid, 3.0 g of vanadium pentoxide and 3 ml of toluene and the temperature of this mixture was enhanced by heating to cause the reaction with stirring at a temperature of about 90° C. for 10 hours.

After the reaction was complete, the product was cooled and cleansed with aqueous sodium bicarbonate solution and then 40.5 g of terephthalaldehyde was obtained by distillation under reduced pressure.

On the other hand, the aqueous sodium bicarbonate solution was acidified to give white crystals. This one was extracted by means of Soxhlet extractor. By removing ether there was obtained 11.4 g of carboxylic acid as by-product.

Yield of terephthalaldehyde corresponds to 75.5% based on $\alpha,\alpha'$-dichloro-p-xylene, $\alpha,\alpha,\alpha'$-trichloro-p-xylene and $\alpha,\alpha,\alpha',\alpha'$-tetrachloro-p-xylene charged.

COMPARATIVE EXAMPLE 1

Reaction of $\alpha,\alpha,\alpha'$-trichloro-p-xylene with 3% by weight of nitric acid was conducted at the same charging conditions as in Example 1 except that the reaction temperature was set at 65° C. The reaction was conducted with stirring at 65° C. for 10 hours, then the stirring was stopped and the reaction mixture separated into oil phase and aqueous phase. On cooling the oil phase solidified. This one was separated and analyzed by gas chromatography, in consequence of which it was, for the great part, starting material $\alpha,\alpha,\alpha'$-trichloro-p-xylene and reaction intermediates, and the amount of terephthalaldehyde formed was as low as corresponding to 8% in the yield based on $\alpha\alpha\alpha'$-trichloro-p-xylene charged.

COMPARATIVE EXAMPLE 2

Charged into the same reactor as used in Example 1 were 84.5 g of mixture with a composition of 20.7% by weight of $\alpha,\alpha'$-dichloro-p-xylene, 49.7% by weight of $\alpha,\alpha,\alpha'$-trichloro-p-xylene and 29.6% by weight of $\alpha,\alpha,\alpha',\alpha'$-tetrachloro-p-xylene, 1700 g of 3% by weight of nitric acid, 3.0 g of ammonium metavanadate and 3 ml of p-xylene. The temperature of this mixture was enhanced by heating to cause the reaction with stirring at a temperature of 65° C. for 10 hours.

When the stirring was stopped after the reaction was complete, the reaction mixture separated into oil phase and aqueous phase. On cooling to room temperature, the oil phase solidified. This solidified substance was separated and analyzed by gas chromatography, in consequence of which terephthalaldehyde was found to be contained therein in the amount of 3.8 g. Yield of terephthalaldehyde corresponds to 7% based on $\alpha,\alpha'$-dichloro-p-xylene, $\alpha,\alpha,\alpha'$-trichloro-p-xylene and $\alpha,\alpha,\alpha',\alpha'$-tetrachloro-p-xylene charged.

EXAMPLE 16

Step 1: Preparation of chloroxylene mixture

Charged into a photoreaction apparatus with an inner capacity of 500 ml equipped with a thermometer, stirrer, chlorine blow tube, reflux condensor functioning also as an exhaust port and light projecting device installed high pressue mercury lamp was 318 g (3 mols) of p-xylene, the contents were heated at 125° C. and dry chlorine was blown in with stirring under the irradiation of light. Shortly after chlorine was blown in, the temperature of the contents was seen to rise with hydrogen chloride generating. Introduction of chlorine was continued for 6 hours at a rate of 1.5 mols/hour under the irradiation of light with the reaction temperature held at 130° C. Hardly any chlorine was recognized in the gas discharged and chlorine blown in reacted nearly completely.

The blowing of chlorine was stopped when 9 mols of chlorine was blown in the reaction for 6 hours and by passing dry nitrogen gas through the reaction solution hydrogen chloride gas and chlorine gas in the system were removed. In this way, the reaction product was obtained in the amount of 623 g.

The analysis of the reaction product by gas chromatography showed the composition to be composed of 0.6 mol % of $\alpha$-chloro-p-xylene, 1.3 mol % of $\alpha,\alpha$-dichloro-p-xylene, 22.5 mol % of $\alpha,\alpha'$-dichloro-p-xylene, 52.9 mol % of $\alpha,\alpha,\alpha'$-trichloro-p-xylene, 18.7 mol % of $\alpha,\alpha,\alpha',\alpha'$-tetrachloro-p-xylene, 1.5 mol % of $\alpha,\alpha,\alpha,\alpha'$-tetrachloro-p-xylene, 1.8 mol % of $\alpha,\alpha,\alpha,\alpha',\alpha'$-pentachloro-p-xylene and 0.7 mol % of others. The average chlorination degree of the reaction solution was 3.0.

Step 2: Reaction of chloroxylene mixture with nitric acid

Charged into a 2 l three neck distillation flask equipped with a thermometer, stirrer and reflux condensor were 84 g (corresponding to 0.40 mol if calculated with the average chlorination degree set at 3.0) of the chloroxylene mixture obtained in Step 1, 1700 g of 3% by weight of nitric acid, 2.5 g of vanadium pentoxide and 3 ml of toluene and the temperature of this mixtur was enhanced by heating with stirring to cause the reaction under refluxed condition for 9 hours.

After the reaction was complete, the reaction product was cooled and crystals formed were filtered off. Then the crystals so filtered off were cleansed with 10% by weight of aqueous sodium bicarbonate solution for about 10 minutes. Carboxylic acid formed as by-product on that occasion moved into the cleansing solution. Crystals of terephthalaldehyde remained undissolved in the aqueous sodium bicarbonate solution were filtered off, washed with water and then dried. In this way, 45.4 g of crystals were obtained. 44.0 g of distillate was obtained from these crystals by distillation under reduced pressure of 15 mmHg. The distillate was analyzed by infrared absorption spectra, in consequence of which this one was identified as terephthalaldehyde. Further, the purity measured by analysis of gas chromatography was 99.4%.

Yield of terephthalaldehyde based on starting material p-xylene was 81%.

Crystals precipitated when the aqueous alkaline solution used in the cleansing of crystals was acidifed. The resultant crystals were filtered off, washed with water and then dried to give 7.8 g of white crystals. The crystals so obtained were extracted by means of Soxhlet extractor using ether as solvent. The ether was distilled off and then 7.4 g of white crystals were obtained. This one was analyzed by infrared absorption spectra, in consequence of which it was identified as 4-carboxybenzaldehyde.

EXAMPLE 17

Charged into the same reactor as used in Step 2 of Example 16 were 84 g of the chloroxylene mixture obtained in Step 1 Example 16, 1700 g of 3% by weight of nitric acid, 5.0 g of $Cu(NO_3)_2.3H_2O$ and 3 ml of p-xylene. The temperature of this mixture was enhanced by heating with stirring to cause the reaction under refluxed condition for 10 hours.

By treating likewise as in Step 2 of Example 16 after the reaction was complete 41.2 g of terephthalaldehyde was obtained as distillates by distillation, and 6.9 g of 4-carboxybenzaldehyde was separated. Yield of terephthalaldehyde was 75.5% based on starting material p-xylene.

EXAMPLE 18

Step 1: Preparation of chloroxylene mixture 318 g (3 mols) of m-xylene was taken in the same photoreaction apparatus as used in Step 1 of Example 16 and the chlorination reaction was conducted by blowing chlorine under the irradiation of light with the reaction temperature held at 130° C. in the same manner as in the case of Step 1 of Example 16. The blowing of chlorine was effected at a rate of 3.0 mols/hour and the reaction was continued for 3 hours. Hardly any chlorine was recognized in the gas discharged and chlorine blown in reacted nearly completely.

The blowing of chlorine was stopped when 9 mols of chlorine was blown in, by passing dry nitrogen gas through the reaction solution hydrogen chloride and chlorine gas in the system were removed and 622 g of reaction solution was obtained.

This one was analyzed by gas chromatography, in consequence of which the composition was found to be composed of 0.6 mol % of $\alpha$-chloro-m-xylene, 1.6 mol % of $\alpha,\alpha$-dichloro-m-xylene, 22.5 mol % of $\alpha,\alpha'$-dichloro-m-xylene, 48.9 mol % of $\alpha,\alpha,\alpha'$-trichloro-m-xylene, 18.7 mol % of $\alpha,\alpha,\alpha',\alpha'$-tetrachloro-m-xylene, 4.1 mol % of $\alpha,\alpha,\alpha,\alpha'$-tetrachloro-m-xylene, 1.8 mol % of $\alpha,\alpha,\alpha,\alpha',\alpha'$-pentachloro-m-xylene and 1.8 mol % of others, the average chlorination degree 3.0.

Step 2: Reaction of chloroxylene mixture with nitric acid

Charged into the same reactor as used in Step 2 of Example 16 were 84 g of the chloroxylene mixture obtained in Step 1, 1700 g of 3% by weight of nitric acid, 3.0 g of ammonium metavanadate and 3 ml of m-xylene. The temperature of this mixture was enhanced by heating with stirring to cause the reaction under refluxed condition for 9 hours.

By treating likewise as in Step 2 of Example 16 after the reaction was complete there was obtained 41.5 g of distillate by distillation. This one was analyzed by infrared absorption spectra, in consequence of which it was identified as isophthalaldehyde. Further, the analysis by gas chromatography showed it to be of 99.2% purity.

Yield of isophthalaldehyde was 76.4% based on starting material m-xylene.

EXAMPLE 19

Step 1: Preparation of chloroxylene mixture 318 g (3.0 mols) of o-xylene was taken in the same photoreaction apparatus as in the case of Step 1 of Example 16 and the chlorination reaction was conducted by blowing chlorine under the irradition of light with the reaction temperature held at 135° C. in the same manner as in Step 1 of Example 16. The blowing of chlorine was effected at a rate of 1.5 mols/hour and the reaction was continued for 6 hours. Hardly any chlorine was recognized in the gas discharged and chlorine blown in reacted nearly completely.

The reaction was finished at the time when 9 mols of chlorine was blown in, by passing dry nitrogen gas through the reaction solution hydrogen chloride and chlorine in the system were removed and then 624 g of reaction solution was obtained.

This one was analyzed by gas chromatography, in consequence of which the composition was found to be composed of 0.5 mol % of α-chloro-o-xylene, 1.1 mol % of α,α-dichloro-o-xylene, 21.2 mol % of α,α'-dichloro-o-xylene, 52.6 mol % of α,α,α'-trichloro-o-xylene, 20.2 mol % of α,α,α',α'-tetrachloro-o-xylene, 1.8 mol % of α,α,α,α'-tetrachloro-o-xylene, 1.1 mol % of α,α,α,α',α'-pentachloro-o-xylene and 1.5 mol % of others, the average chlorination degree of the reaction solution 3.0.

Step 2: Reaction of chloroxylene mixture with nitric acid

Charged into the same reactor as used in the case of Step 2 of Example 16 were 84.0 g of the chloroxylene mixture obtained in Step 1, 1700 g of 3% by weight of nitric acid and 2.0 g of vanadium pentoxide. The temperature of this mixture was enhanced by heating with stirring to cause the reaction under refluxed condition for 6 hours.

After the reaction was complete, the reaction product was cooled and subjected to 4 times of extraction operations by the addition of 300 g of toluene for each time. Toluene, which went through the extraction operations, was put together, it was cleansed with aqueous sodium bicarbonate solution and then toluene was distilled off. As a result, 42.8 g of residue was obtained. 41.0 g of distillate was obtained from this one by distillation under reduced pressure of 10 mmHg. This distillate was analyzed by infrared absorption spectra, in consequence of which it was identified as phthalaldehyde containing traces of phthalide. Further, the analysis by gas chromatography showed it to be of 99.1% purity. Yield of phthalaldehyde was 75.7% based on o-xylene being starting material for the distillate.

EXAMPLE 20

Step 1: Preparation of chloroxylene mixture

By using the photoreaction apparatus with an inner capacity of 500 ml equipped with a high pressure mercury lamp installed light projecting device, thermometer, stirrer, reflux condenser functioning also as an exhaust port, chlorine blow port, xylene and recycling solution feed ports and reaction solution flooding port and reaction apparatus composed of a reaction solution storage tank, degassing tank, distillation column (22×1800 mm, filled with 3 mm φ porcelain Raschig rings) and distillation column distillate storage tank the continuous chlorination reaction of p-xylene was conducted in the following manner.

That is, the reactor, reaction solution storage tank and degassing tank were filled in advance with the reaction solution obtained by reacting 1 mol of chlorine per mol of p-xylene under the irradiation of light and then the chlorination reaction was conducted at the reaction temperature of 135° C. under the irradiation of light while p-xylene was continuously fed at a rate of 3 g (0.5 mol) per hour and chlorine at a rate of 88.6 g (1.25 mols) per hour to the reactor. The increased content of the reaction solution which was caused to increase due to p-xylene and chlorine fed to the reactor was led to the reaction solution storage tank from the flooding port. Then it was led to the degassing tank with the temperature held at 100° C. and pressure at 200 mmHg, where hydrogen chloride gas dissolved therein was removed, and it was fed to the distillation column. The distillation column was held at 23 mmHg in the overhead pressure and p-xylene, α-chloro-p-xylene and α,α-dichloro-p-xylene were taken overhead and α,α'-dichloro-p-xylene, α,α,α'-trichloro-p-xylene and high boiling substances were withdrawn from the bottom. Distillates taken overhead were recycled to the reactor by way of the distillate storage tank.

Operation was effected until the reaction solution composition reached a stationary condition by following such procedures and the amount of chlorides taken out of the system from the bottom of distillation column when stationary was 97.4 g per hour and analysis of this one by gas chromatography showed the composition to be composed of 1.1 mol % of α,α-dichloro-p-xylene, 52.5 mol % of α,α'-dichloro-p-xylene, 39.3 mol % of α,α,α'-trichloro-p-xylene, 5.2 mol % of α,α,α',α'-tetrachloro-p-xylene and 1.9 mol % of others, the average chlorination degree of this one 2.5.

Step 2: Reaction of chloroxylene mixture with nitric acid

Charged into the same reaction apparatus as used in Step 2 of Example 16 were 77 g of the chloroxylene mixture obtained in Step 1, 1700 g of 3% by weight of nitric acid, 2.5 g of vanadium pentoxide and 3 ml of p-xylene and the temperature of the mixture was enhanced by heating with stirring to cause the reaction under refluxed condition for 9 hours.

By treating likewise as in Step 2 of Example 16 after the reaction was complete there were obtained 44.2 g of terephthalaldehyde and 7.5 g of 4-carboxybenzaldehyde after distillation. Yield of terephthalaldehyde was 83.3% based on starting material p-xylene.

EXAMPLE 21

Charged into the same reactor as used in Step 2 of Example 16 were 84 g of the chloro-p-xylene mixture obtained in Step 1 of Example 16, 1700 g of 3% by weight of nitric acid, 3.0 g of vanadium pentoxide and 3 ml of toluene and the temperature of this mixture was enhanced by heating to cause the reaction under stirring for 10 hours with the temperature of the contents held at 88° C.

By treating likewise as in Step 2 of Example 16 after the reaction was complete there were obtained 36.3 g of terephthalaldehyde and 13.8 g of carboxylic acid as by-product as distillates by distillation. Yield of terephthalaldehyde corresponds to 66.9% based on starting material p-xylene.

COMPARATIVE EXAMPLE 3

Step 1: Preparation of chloroxylene mixture

By using the same photoreaction apparatus as used in Step 1 of Example 16 the reaction of 318 g (3 mols) of p-xylene with 383 g (5.4 mols) of chlorine was conducted in the same manner as in Step 1 of Example 16. After the reaction was finished, dry nitrogen gas passed through to remove hydrogen chloride and chlorine from the system. Then 501 g of reaction solution was obtained. This one was analyzed by gas chromatography, in consequence of which the composition was found to be composed of 2.3 mol % of p-xylene, 30.3 mol % of α-chloro-p-xylene, 8.9 mol % of α,α-dichloro-p-xylene, 46.0 mol % of α,α'-dichloro-p-xylene, 11.7 mol % of α,α,α'-trichloro-p-xylene, 0.4 mol % of α,α,α',α'-tetrachloro-p-xylene and 0.4 mol % of others, the average chlorination degree for p-xylene of the reaction solution 1.8.

Step 2: Reaction of chloroxylene mixture with nitric acid

Charged into the same reactor as used in Step 2 of Example 16 were 70.0 g of the chloroxylene mixture obtained in Step 1, 1700 g of 3% by weight of nitric acid, 2.5 g of vanadium pentoxide and 3 ml of toluene and the temperature of this mixture was enhanced by heating with stirring to conduct the reaction under refluxed condition for 9 hours.

By treating likewise as in Step 2 of Example 16 after the reaction was complete there was obtained 27.7 g of terephthalaldehyde. Yield of terephthalaldehyde was 49.3% based on starting material p-xylene.

COMPARATIVE EXAMPLE 4

Step 1: Preparation of chloroxylene mixture

By using the same photoreaction apparatus as in Step 1 of Example 16 the reaction of 318 g (3 mols) of p-xylene with 905 g (12.75 mols) of chlorine was conducted in the same manner as in Step 1 of Example 16. After the reaction was finished dry nitrogen gas was passed through to remove hydrogen chloride and chlorine gas from the system. Then 748 g of reaction solution was obtained. This one was analyzed by gas chromatography, in consequence of which the composition was found to be composed of 14.5 mol % of α,α,α'-trichloro-p-xylene, 53.5 mol % of α,α,α',α'-tertrachloro-p-xylene, 5.0 mol % of α,α,α,α'-tetrachloro-p-xylene, 23.8 mol % of α,α,α,α',α'-pentachloro-p-xylene, 1.2 mol % of α,α,α,α',α',α'-hexachloro-p-xylene and 2.0 mol % of others, the average chlorination degree for p-xylene of the reaction solution 4.1.

Step 2: Reaction of chloroxylene mixture with nitric acid

Charged into the same reactor as used in Step 2 of Example 16 were 99.0 g of the chloroxylene mixture obtained in Step 1, 1700 g of 3% by weight of nitric acid, 2.5 g of vanadium pentoxide and 3 ml of toluene and the temperature of this mixture was enhanced by heating with stirring to cause the reaction under refluxed condition for 9 hours.

By treating likewise as in Step 2 of Example 16 there was obtained 29.7 g of terephthalaldehyde. Yield of terephthalaldehyde was 55.8% based on starting material p-xylene.

COMPARATIVE EXAMPLE 5

Charged into the same reactor as used in Step 2 of Example 16 were 84 g of the chloroxylene mixture obtained in the same manner as in Step 1 of Example 16, 1700 g of 3% by weight of nitric acid, 3.0 g of vanadium pentoxide and 3 ml of toluene and the temperature of this mixture was enhanced by heating to cause the reaction under stirring for 10 hours with the temperature of the contents held at 65° C.

After the reaction was finished the stirring was stopped and the reaction mixture separated into oil phase and aqueous phase. Upon cooling to room temperature the liquid phase was seen to solidify. This solidified substance weighed 51 g and it was analyzed by gas chromatography and the content of terephthalaldehyde was found to be 6% by weight. Yield of terephthalaldehyde corresponds to 5.6% based on starting material p-xylene.

What we claim is:

1. A process for the production of aromatic dialdehydes which comprises reacting 0.2 to 20 moles of xylene chloride with 0.5–15% by weight of nitric acid at temperatures of 70°–130° C. at pressure ranging from normal pressure up to 3 kg/cm$^2$, said xylene chloride selected from the group consisting of α,α,α'-trichloroxylene alone, or a mixture of α,α,α'-trichloroxylene and α,α'-dichloroxylene; a mixture of α,α,α'-trichlorixylene and α,α,α',α'-tetrachloroxylene and a mixture of α,α,α'-trichloroxylene, α,α'-dichloroxylene and α,α',α,α'-tetrachloroxylene, said reaction being carried with or without the presence of a catalyst, such that when a catalyst is used the time of reaction is 3–10 hours and when no catalyst is used the time of reaction is 10–20 hours and the catalyst, when present, is a compound of a metal of atomic number from 23–29.

2. The process according to claim 1 in which the reaction is carried out at temperatures of 70°–110° C. under normal pressure.

3. The process according to claim 1 in which the reaction is carried out in the presence of a catalyst selected from the group consisting of vanadium pentoxide, vanadium chloride, vanadyl sulphate or ammonium metavanadate.

* * * * *